United States Patent [19]

Pilgram et al.

[11] Patent Number: 4,587,259

[45] Date of Patent: May 6, 1986

[54] MITICIDAL 2-(2-METHYL-2,3-DIHYDRO-BENZOFURAN-7-YL)HYDRAZINECARBOXYLIC ACID ESTERS

[75] Inventors: Kurt H. Pilgram; Richard D. Skiles, both of Modesto, Calif.

[73] Assignee: Shell Oil Company, Houston, Tex.

[21] Appl. No.: 626,556

[22] Filed: Jun. 29, 1984

[51] Int. Cl.$^4$ .................... A01N 47/24; C07D 307/79
[52] U.S. Cl. ...................................... 514/469; 549/462
[58] Field of Search ......................... 549/462; 514/469

[56] References Cited

FOREIGN PATENT DOCUMENTS 48040 3/1982 European Pat. Off. .
67471 12/1982 European Pat. Off. .

Primary Examiner—Henry R. Jiles
Assistant Examiner—Bernard I. Dentz

[57] ABSTRACT

Certain miticidal 2-(2-alkyl-2,3-dihydro-benzofuran-7-yl)-hydrazinecarboxylic acid esters.

5 Claims, No Drawings

MITICIDAL 2-(2-METHYL-2,3-DIHYDRO-BENZOFURAN-7-YL)HYDRAZINECARBOXYLIC ACID ESTERS

DESCRIPTION OF THE INVENTION

It has been found that certain 2-(2-methyl-2,3-dihydrobenzofuran-7-yl)hydrazinecarboxylic acid esters are toxic with respect to mites that feed upon plants.

These miticides are described by the generic formula:

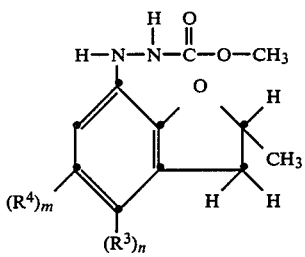

wherein $R^3$ and $R^4$ each is bromine, chlorine, or methyl, m is zero or one, n is zero or one, with the proviso that m+n=1 or 2.

Compounds of Formula I can be prepared by treating the appropriate 7-hydrazino-2,3-dihydro-benzofuran with the appropriate methyl chloroformate in the presence of a tertiary amine as hydrogen chloride acceptor. The reaction proceeds according to the equation:

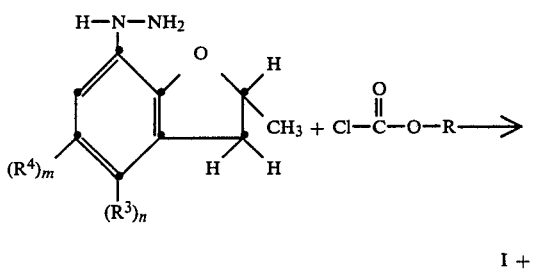

I + HCl

The reaction can be effected by slowly adding one of the reagents to a stirred solution of the other reagent in an inert solvent (tetrahydrofuran is a typical example) in the presence of the amine at a low temperature—for example −5° C. to 0° C., then if necessary warming the mixture or even heating it at reflux temperature for a time sufficient to ensure completion of the reaction. The formula I species is isolated from the reaction mixture, and purified, by conventional means, as is shown in particular instances in the Examples, hereinafter. Methyl chloroformate is a known and readily available material. A suitable hydrogen chloride acceptor in many instances is N,N-diisopropylethylamine; triethylamine and pyridine are also suitable.

The 7-hydrazino-2,3-dihydro-benzofuran (II) is prepared from the corresponding 7-nitro-2,3-dihydro-benzofuran according to the reactions expressed by the equations A—NO₂ (III)  A—NH₂ (IV) ⟶

A—N=N—SO₃Na (V) ⟶ A—NHNHSO₃K (VI) ⟶ II wherein A represents

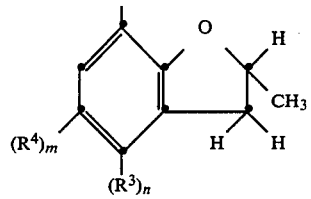

Intermediate IV is prepared by conventional Raney nickel-catalyzed hydrogenation in a Parr shaker of a solution of intermediate III in an inert solvent such as tetrahydrofuran. Intermediate V is prepared by diazotizing intermediate IV, followed by treatment with sodium sulfite. The diazotization is conventional, effected by treating IV with concentrated hydrochloric acid at about room temperature, diluting the mixture with water, cooling it to about 0° C. and slowly adding an aqueous solution of sodium nitrite to the stirred mixture. Then the resulting diazonium salt solution is added to a cold aqueous solution/suspension of sodium sulfite, and the resulting mixture is stirred at room temperature to complete the reaction. Intermediate V may be isolated and further treated, or the crude product may be used to prepare intermediate VI. In either case, aqueous V is treated with sodium dithionite (added in portions to the stirred mixture at room temperature), then potassium chloride is added and the mixture is stirred at a moderately elevated temperature (for example, 60°–80° C.) for a time sufficient to complete the reaction. Intermediate VI is recovered by filtering the mixture. VI then can be converted to intermediate II by mixing it with a lower alkanol, such as methanol, treating the cold (0° C.) mixture with hydrogen chloride, evaporating the alkanol, treating the residue with aqueous sodium hydroxide, and extracting the resulting II, using a suitable solvent.

The 7-nitro-2,3-dihydrobenzofuran precursors can be prepared from the appropriate 2-nitrophenol by the general procedures described in U.S. Pat. No. 3,412,110 for the preparation of a similar 2,3-dihydrobenzofuran: an alkali metal (M) salt of the phenol (VII) is treated with the appropriate 3-halo-1-alkene, the resulting 1-(2-alk-2-enyloxy)-2-nitrobenzene (VIII) is Claisen-rearranged to form the corresponding 2-(2-alk-2-enyl)-6-nitrophenol (IX), which is ring-closed to form the 7-nitro-2,3-dihydrobenzofuran precursor (III).

The reactions proceed according to the equations:

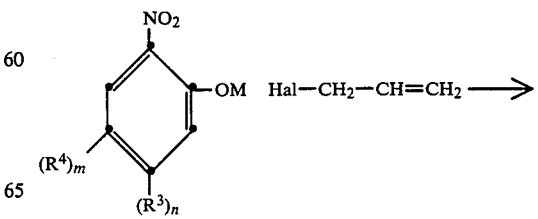

(VII)

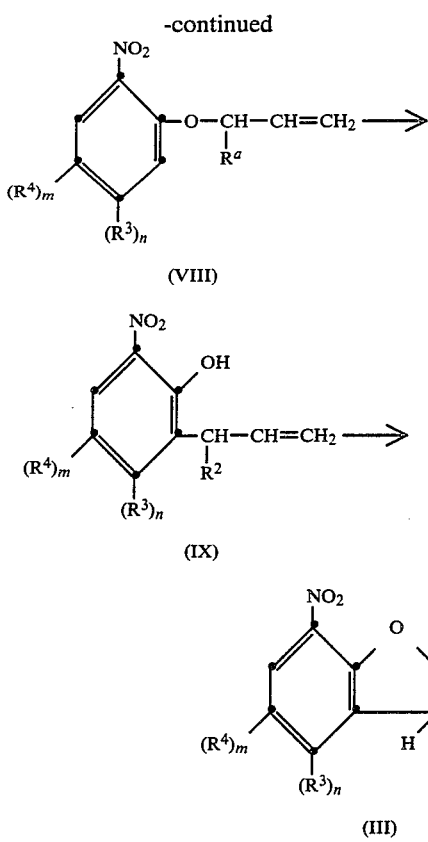

Conversion of VII to VIII can be effected by treating a solution of the phenol (VII), in a solvent such as dimethyl sulfoxide, with an alkali metal base such as sodium hydroxide or sodium hydride, in the presence of, or subsequently treating the alkali metal phenoxide thus formed with the appropriate alkenyl halide, then heating the resulting mixture at a moderately elevated temperature, for example, 80°–120° C.

Claisen-rearrangement of VIII is effected conventionally—conveniently by heating VIII to a moderately elevated temperature—e.g., 150°–250° C.—in an inert atmosphere.

Ring closure of IX is effected by heating it in the presence of an acid. Suitable acids include the mineral acids, such as hydrochloric, hydrobromic, sulfuric and phosphoric acids. The hydrohalide acids are to be preferred since they have less tendency to cause side-reactions to occur. An organic acid such as acetic acid can also be utilized—and may be used as reaction medium when a mineral acid is used. Ordinarily, the acid is employed as an aqueous solution.

It must be noted that in some cases hydrobromic acid will not be suitable, because at least in part it will add to the double bond, giving the bromoalkyl derivative rather than effecting the cyclization. In such a case, cyclization can be effected by use of a less-reactive acid, such as hydrochloric acid.

The preparation, isolation and physical properties of typical individual species of the compounds of Formula I, in particular instances, are described in the following examples. In each case, the identity of the product, and each of any intermediate involved, was confirmed by appropriate chemical and spectral analyses.

EXAMPLE 1

2-(2,3-Dihydro-2,4-dimethylbenzofuran-7-yl)hydrazinecarboxylic Acid Methyl Ester (1)

A solution of 26.1 g of sodium hydroxide in 50 ml of water was added drop-by-drop over 5 minutes to a stirred mixture of 100 g of 3-methyl-6-nitrophenol, 400 ml of dimethylsulfoxide (DMSO) and 53.6 g of 3-chloro-1-propene initially at room temperature. The temperature of the mixture rose to 43° C. The mixture was heated at 90°–110° C. for two hours, poured into water and filtered, to give 1-(2-propenyloxy)-3-methyl-6-nitrobenzene (1A), as a light yellow solid, m.p.: 30°–32° C.

1A was placed in a flask, which then was purged with nitrogen, and a slow stream of nitrogen was passed through the system while the 1A was heated to 185°–205° C. and stirred at that temperature for 2.5 hours. The mixture was cooled to 25° C., diluted with 400 ml of ether and filtered through Celite. The solvent was evaporated from the filtrate to give 2-(2-propenyl)-3-methyl-6-nitrophenol (1B), as an amber syrup.

47 g of 1B was added to a mixture of 100 ml of glacial acetic acid and 100 ml of 48% aqueous hydrobromic acid and the mixture was heated at 114°–115° C. for 2.5 hours. The resulting mixture was stripped to dryness, the residue was taken up in 500 ml of ether, and filtered. The filtrate was concentrated to 100 ml, 300 ml of hexane was added, the mixture was chilled and filtered to give 2,3-dihydro-2,4-dimethyl-7-nitrobenzofuran (1C), as a tan solid, m.p.: 69°–71° C.

A mixture of 24.3 g of 1C, 200 ml of tetrahydrofuran (THF) and 2 g of activated Raney nickel catalyst was treated with hydrogen (40 psig) in a Parr shaker three hours, then filtered. The solvent was evaporated from the filtrate to give 7-amino-2,3-dihydro-2,4-dimethylbenzofuran (1D), as an amber syrup.

A mixture of 50 ml of concentrated hydrochloric acid and 19.8 g of 1D was stirred, warmed to 80° C. and allowed to stand at room temperature for 18 hours. Then 50 ml of ice water was added, the mixture was cooled to 0° C. and stirred while a solution of 9.6 g of sodium nitrite in 20 ml of water was added drop-by-drop over 15 minutes to the cold stirred mixture. The cold mixture was stirred for an additional hour and then was added to a cold stirred mixture of 100 g of sodium sulfite in 180 ml of water. The resulting mixture was stirred at room temperature for six hours, then 21.9 g of sodium dithionite was added, in portions. The resulting mixture was stirred at room temperature for 18 hours, then at 75° C. while 150 g of potassium chloride was added. The resulting mixture was stirred at 75° C. for 30 minutes, then at room temperature for two hours, then was cooled to 5° C. and filtered. The filter cake was air dried, mixed with 400 ml of methanol, the mixture was chiled to 0° C. and an excess of anhydrous hydrogen chloride was added. The methanol was evaporated under reduced pressure, the residue taken up in water, 50% aqueous sodium hydroxide solution was added, and the resulting mixture was extracted with ether. The extract was dried (MgSO₄), filtered and the solvent was evaporated to give 2,3-dihydro-2,4-dimethyl-7-hydrazinobenzofuran (1E), as an amber syrup.

15.6 g of 1E was mixed with 150 ml of THF and 11.3 g of N,N-diisopropylethylamine. The mixture was cooled to −5° C. and 9.1 g of methyl chloroformate was added drop-by-drop to the stirred mixture, which then was stirred at 0° C. for two hours. The mixture then was poured over ice water and extracted with ether. The extract was dried (MgSO$_4$), filtered and the solvent was evaporated. The residue was column chromatographed on silica gel, using a 1:4:20 v:v:v mixture of tetrahydrofuran, ethyl acetate and hexane as eluent, to give 1, as a tan solid, m.p.: 90°–92° C.

EXAMPLE 2

2-(2,3-Dihydro-2,5-dimethylbenzofuran-7-yl)hydrazinecarboxylic acid methyl ester (2) was prepared as a tan solid, m.p.: 92°–94° C., from 4-methyl-2-nitrophenol, and 3-chloropropene according to the procedures described in Example 1.

EXAMPLE 3

2-(4-Chloro-2,3-dihydro-2,5-dimethylbenzofuran-7-yl)hydrazinecarboxylic Acid Methyl Ester (3)

283.0 g of 3-chloro-4-methylaniline, 1000 ml of water and 500 ml of concentrated sulfuric acid were mixed, initially at room temperature. The temperature of the mixture rose to 95° C. The mixture was stirred at room temperature for 30 minutes, cooled to 5° C. and a solution of 145 g of sodium nitrite in 500 ml of water was slowly added (1.5 hours) to the stirred mixture at 5°–10° C., then the mixture was stirred at about 5° C. for one hour. The resulting solution was added over two hours to a stirred solution of 1.2 liters of concentrated sulfuric acid in 2 liters of water, at 105°–110° C., and the resulting mixture was stirred at 110° C. for one hour, then held at room temperature for 18 hours. Then 3.5 liters of hexane was added, the mixture was stirred for 30 minutes, allowed to stand, and the two liquid phases were separated. The hexane phase was filtered, washed with water, dried (MgSO$_4$) and concentrated to dryness to give crude (91%) 3-chloro-4-methylphenol (3A).

245.0 g of 3A was mixed with 1.6 liters of glacial acetic acid, and the resulting solution was stirred at 8°–10° C. while 109.6 g of 90% aqueous nitric acid was added (two hours). The mixture was stirred at 10°–15° C. for five hours, poured over ice water and extracted with ether/hexane. The extract was washed with water, dried and stripped to dryness. The residue was stirred with 3 liters of hexane and the hexane solution was filtered through silica gel. The filtrate was held at −20° C. for 16 hours, filtered, and the filtrate was concentrated to one liter, charcoaled, then held at −30° to −35° C. for two hours and filtered. The solid products were combined to give 3-chloro-4-methyl-6-nitrophenol (3B).

A mixture of 93.4 g of 3B, 750 ml of DMSO, 48 g of 50% aqueous sodium hydroxide and 45.9 g of 3-chloro-1-propene was stirred for 8 hours at 75°–80° C., then for 16 hours at room temperature, was mixed with 3 liters of ice water and the resulting mixture was extracted with methylene chloride. The extract was washed with water, dried (MgSO$_4$) and evaporated to dryness. The residue was placed in a flask purged with nitrogen, in a nitrogen atmosphere was heated slowly to 190° C. (one hour) and held at 185°–195° C. for two hours, cooled to room temperature, and dissolved into 250 ml of acetic acid. To this solution 150 ml of 48% aqueous hydrogen bromide solution was added, the mixture was stirred at reflux for three hours, mixed with 2 liters of ice water and the resulting mixture was extracted with a 1:1 v:v mixture of hexane and ether. The extract was washed with water, 5% aqueous sodium bicarbonate solution, dried (MgSO$_4$), charcoaled and concentrated to dryness. The residue was crystallized from 500 ml of 9:1 v:v hexane/ether mixture, giving 2,3-dihydro-2,5-dimethyl-4-chloro-7-nitrobenzofuran (3C), m.p.: 114°–116° C.

51.0 g of 3C was dissolved in 600 ml of THF. The solution was divided in half, and each half was hydrogenated (40–50 psig hydrogen pressure) in the presence of 1 g of palladium-on-charcoal catalyst. The final combined reaction mixtures were filtered, the filtrates were combined, dried (MgSO$_4$) and evaporated to dryness, to give 7-amino-2,3-dihydro-2,5-dimethyl-4-chlorobenzofuran (3D).

19.75 g of 3D, 200 ml of water and 100 ml of concentrated hydrochloric acid were mixed, cooled to 0° C. and a solution of 7.3 g of sodium nitrite in 50 ml of water was slowly added (one hour) to the stirred mixture at 0°–5° C. The mixture was stirred at 25° C. for one hour, then 55.2 g of potassium carbonate was slowly added (one hour) at about 5° C. The resulting mixture was cooled to 0° C. and slowly added (over 30 minutes) to a solution of 50.4 g of sodium sulfite in 300 ml of water at 5°–10° C. The mixture was stirred at 5°–10° C. for three hours, and at room temperature for 16 hours. Then 20.9 g of sodium dithionite was added, the mixture was stirred at room temperature for two hours, then 80° C. for 15 minutes. Then 200 g of potassium chloride was added, the mixture was cooled and stirred at 5° C. for two hours, filtered and the collected solid was air-dried. The solid then was mixed with 250 ml of methanol, and with stirring and cooling (5°–15° C.), 5 g of anhydrous hydrogen chloride was bubbled into the mixture, which then was stirred at room temperature for three hours. The methanol was evaporated under reduced pressure, at 30°–40° C. The residue was added to 500 ml of ice water and 10 g of 50% aqueous sodium hydroxide solution. The resulting mixture was extracted with ether, the extract was dried (MgSO$_4$) and evaporated to dryness. The residue was dissolved in 200 ml of tetrahydrofuran and 12.9 g of N,N-diisopropylethylamine was added. The mixture was stirred at 5° C. while 5.7 g of methyl chloroformate was added over 15 minutes at 5°–10° C. The mixture was poured into ice water and extracted with ether. The extract was dried (MgSO$_4$) and evaporated to dryness. The residue was washed with 1:1 v:v ether/hexane mixture and dried, to give 3, as a white solid, m.p.: 157°–160° C.

EXAMPLE 4

2-(2,3-Dihydro-5-chloro-2,4-dimethylbenzofuran-7-yl)hydrazinecarboxylic Acid Methyl Ester (4)

4 was prepared, as tan solid, m.p.: 152°–154° C., from 4-chloro-6-nitro-m-cresol and 3-bromo-1-propene by the procedures described in Example 3 for the preparation of 1 from 3-methyl-6-nitrophenol.

Compounds of Formula I have been found to be toxic to mites that feed on plants, with little or no toxicity to other pests which feed on plants. Compounds of Formula I have been found to be effective with respect to resistant mites as well as to susceptible mites.

Accordingly, the invention includes a method for combatting plant-feeding mites which comprises applying to the foliage of the plants to be protected an effective amount of a compound of Formula I.

for application, the compound of the invention ordinarily is applied most effectively by formulating it with a suitable inert carrier or surface-active agent, or both. The invention, therefore, also includes compositions suitable for combatting mites, such compositions comprising an inert carrier or surface-active agent, or both, and as active ingredient at least one compound of the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25–75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3–7% by weight of a blend of surfactants, which act as wetting, dispersing, suspending and binding agents, and 1–3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control mites comprises applying the compound, ordinarily in a composition of one of the aforementioned types, to a locus or area to be protected from the mites, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the mite contacts—is of the order of 0.001 to 0.5% based on the total weight of the formulation, though under some circumstances the effective concentration will be as little as 0.0001% or as much as 2%, on the same basis.

It has been found that the stability of compounds of this invention may be adversely affected by some surfactants, resulting in decomposition of such compounds during storage of the formulation containing the surfactant. Also, it appears that the stability of compounds of the invention may be adversely affected by mineral carriers. This characteristic of the compounds of the invention must be taken into account when formulating them.

MITICIDAL ACTIVITY

Toxicity of compounds of this invention with respect to mites were determined as follows:

Adult female two-spotted spider mites (*Tetranychus urticae* (Koch)) were tested by placing 50-75 mites on the bottom side of leaves of pinto bean plants. The leaves were sprayed with dilutions of acetone solution of test compound into water containing an emulsifier and kept under laboratory conditions for about 20 hours at which time mortality counts were made. The tests were conducted employing several different dosage rates of test compounds.

In each set of tests, identical tests were conducted using Parathion as a standard for comparison.

In each instance, the toxicity of the test compound was compared to that of the standard pesticide (Parathion), its relative toxicity then being expressed in terms of the relationship between the amount of the test compound and the amount of the standard pesticide required to produce the same percentage (50%) of mortality in the mites. By assigning the standard pesticide an arbitrary rating of 100, the toxicities of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 would be twice as active, as the standard pesticide. The results are set forth in Table I.

TABLE I

| Compound Number | Toxicity Index, Two-Spotted Spider Mites |
|---|---|
| 1 | 290 |

TABLE I-continued

| Compound Number | Toxicity Index, Two-Spotted Spider Mites |
|---|---|
| 2 | 290 |
| 3 | 120 |
| 4 | 390 |

In similar standardized tests, compounds of Formula I were found to have little or no toxicity with respect to houseflies, pea aphids, and corn earworms.

In a similar standardized tests, Compound 1 was found to be about as toxic with respect to a strain of two-spotted spider mites that are resistant to organophosphorus insecticides as with respect to a strain of two-spotted spider mites that are not so resistant.

In addition to their utility as miticides, compounds of Formula I also have utility as precursors for the miticidal and insecticidal compounds of copending application Ser. No. 643,329.

We claim:

1. A compound of the formula

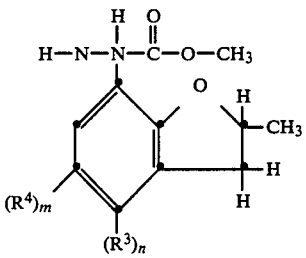

wherein m and n each is one, one of $R^3$ and $R^4$ is methyl and the other is chlorine.

2. A compound according to claim 1 wherein $R^3$ is methyl and $R^4$ is chlorine.

3. A compound according to claim 1 wherein $R^3$ is chlorine and $R^4$ is methyl.

4. A method for protecting a plant from mites that comprises applying to the plant a miticidally effective dosage of a compound of the formula:

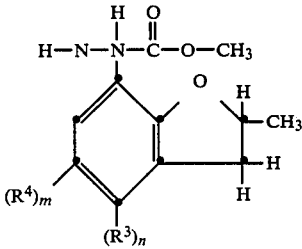

wherein $R^3$ and $R^4$ each is bromine, chlorine or methyl, m is zero or one, n is zero or one, with the proviso that m+n=one or two.

5. A method according to claim 4 wherein the compound is one in which $R^3$ is methyl and $R^4$ is chlorine.

* * * * *